United States Patent [19]

Onopchenko et al.

[11] 4,352,942
[45] Oct. 5, 1982

[54] PURIFICATION PROCESS

[75] Inventors: Anatoli Onopchenko, Monroeville; Edward T. Sabourin, Allison Park; Charles M. Selwitz, Monroeville, all of Pa.

[73] Assignee: Gulf Research & Development Company, Pittsburgh, Pa.

[21] Appl. No.: 242,692

[22] Filed: Mar. 11, 1981

[51] Int. Cl.³ .................. C07C 49/213; C07C 49/215
[52] U.S. Cl. ............................... 568/306; 260/465 R; 260/465 H
[58] Field of Search ............................... 568/305, 306; 260/465 R, 465 H

[56] References Cited

U.S. PATENT DOCUMENTS

| | | | |
|---|---|---|---|
| 3,280,200 | 10/1966 | Greer | 568/306 |
| 3,869,513 | 3/1975 | Buckman et al. | 568/306 |
| 3,983,156 | 9/1976 | Buckle et al. | 568/306 |

*Primary Examiner*—Natalie Trousof
*Assistant Examiner*—Vera C. Clarke
*Attorney, Agent, or Firm*—Deane E. Keith; Forrest D. Stine; Joseph J. Carducci

[57] ABSTRACT

A process for reducing the amount of ortho nitro aromatic keto compounds in a mixture containing the same which comprises contacting such mixture with oleum.

16 Claims, No Drawings

PURIFICATION PROCESS

BACKGROUND OF THE INVENTION

1. Field of the Invention

The present invention is directed to a process for reducing the amount of ortho nitro aromatic keto compounds in a mixture containing the same which comprises contacting such mixture with oleum.

2. Description of the Prior Art

Ortho nitro aromatic keto compounds can be found in mixtures wherein their presence is not desired and, obviously, reducing their presence therein, or better still, reducing them entirely, would be highly desirable. For example, diaminobenzophenones, obtained by nitrating benzophenone with nitric acid and thereafter subjecting the resulting dinitrobenzophenones to hydrogenation, can be reacted with a dianhydride, such as 3,4,3',4'-benzophenone tetracarboxylic dianhydride (BTDA) to obtain a polyimide. When the benzophenone is reacted with nitric acid to form the dinitrobenzophenone, a mixture of isomers can be formed, for example, o,o'-dinitrobenzophenone, o,m'-dinitrobenzophenone, o,p-dinitrobenzophenone, m,m'-dinitrobenzophenone, m,p'-dinitrobenzophenone and p,p'-dinitrobenzophenone. Although the m,m'-, m,p'- and p,p'-diamino benzophenones obtained from said mixture will react satisfactorily with BTDA to form desired long-chain polyimide resins, the diaminobenzophenones containing an ortho amine substituent will react with BTDA to a lesser extent, resulting in a mixture of long and relatively short polyimide resins. This is believed to be the result of hydrogen bonding between an ortho amine hydrogen and the carbonyl which reduces the basicity of the compound and renders the compound less reactive with BTDA. It would be highly desirable, therefore, to reduce the content of an ortho nitro aromatic keto compound containing the same.

SUMMARY OF THE INVENTION

We have discovered that the ortho nitro aromatic keto content of a mixture containing the same can be reduced by contacting said mixture with oleum.

The ortho nitro aromatic keto compounds, or mixtures of such compounds, referred to above, can be defined, for example, in accordance with the following formula (A):

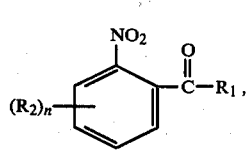

wherein $R_1$ can be an alkyl radical having from one to 10 carbon atoms, preferably from one to four carbon atoms, such as methyl, ethyl, n-propyl, isopropyl, n-butyl, t-butyl, secbutyl, isobutyl, neo-pentyl, n-decyl, etc., an aryl radical having from six to 20 carbon atoms, preferably from six to 10 carbon atoms, such as phenyl, naphthyl, p-tolyl, m-tolyl, o-tolyl, m-chlorophenyl, o-bromophenyl, m-nitrophenyl, p-nitrophenyl, etc.; or an aroyl radical having from six to 20 carbon atoms, preferably from six to 10 carbon atoms, such as benzoyl, m-nitrobenzoyl, p-nitrobenzoyl, m-chlorobenzoyl, p-bromobenzoyl, etc.; $R_2$ can be a halogen, such as chloro, bromo, iodo and fluoro, nitro, cyano, or alkyl, aryl or aroyl radicals, as defined above; and n is an integer ranging from 0 to 4, generally from 0 to 2. Specific examples of such compounds include o-nitrobenzophenone, o-nitro-p'-chlorobenzophenone, o,o'-dinitrobenzophenone, o,m'-dinitrobenzophenone, o,p'-dinitrobenzophenone, o-nitroacetophenone, o-nitrobenzil, o-nitro-p'-benzoylbenzophenone, o-nitro-m'-chlorobenzophenone, o-nitro-p'-bromobenzophenone, o-nitro-m' methylbenzophenone, 2-nitro-4,4'-dimethylbenzophenone, 2,2'-dinitro-4,4'-dichlorobenzophenone, 2-nitro-5-chloroacetophenone, 2,4-dinitroacetophenone, 2-nitro-4,5,3',4'-tetramethylbenzophenone, 2-nitro-3'-cyanobenzil, etc.

The second component (B) of the mixture being treated herein can be composed of one or more compounds that are substantially inert or unreactive when contacted with oleum under the conditions of temperature and time defined hereinafter. Generally, the second component (B) will be composed of one or more compounds similar to component (A), defined above, but wherein no nitro substituent is present ortho to the keto carbonyl. Specific examples of compounds that can be defined as component (B) include p-nitrobenzophenone, m-nitrobenzophenone, m,m'-,m,p'-dinitro-, and p,p'-dinitrobenzophenones, m-nitro-and p-nitroacetophenones, m-nitro- and p-nitrobenzils, m-nitro-m'-chloro- and m-nitro-p'-chlorobenzils, m-nitro-m'-bromobenzophenones, p-nitro-p'-bromobenzophenone, m-nitro-m'-benzoylbenzophenone, m-nitro-m'-(3-nitrobenzoyl)-benzophenone, etc.

The weight ratio of component (A) to component (B) can vary over a wide range, for example, from about 0.1:99.9 to about 60:40, but, in general, the weight ratio will be in the range of about 5:95 to about 40:60.

As mentioned above, the defined mixture is contacted with oleum to reduce the ortho nitro aromatic keto content thereof. By "oleum" we mean to include concentrated sulfuric acid (100 weight percent sulfuric acid) containing sulfur trioxide. The amount of sulfur trioxide, on a weight basis relative to the total weight of sulfuric acid and sulfur trioxide, will be in the range of about five to about 65 percent, preferably about 10 to about 35 percent. Oleum suitable for use herein can be prepared, for example, by adding gaseous or liquid $SO_3$ to concentrated sulfuric acid. It is believed that sulfur trioxide when dissolved, or added to, in sulfuric acid readily forms $H_2S_2O_7$ and higher polysulfuric acids [R. Gillespie, *J. Chem. Soc.*, 2493 (1950)].

In carrying out the process defined herein the oleum and the mixture being treated are admixed in a weight ratio of about 1:1 to about 25:1, but preferably in a weight ratio of about 2:1 to about 5:1. During such contact, which can be about 0.1 to about 48 hours, generally in the range of about 0.5 to about six hours, the temperature of the reaction mixture is maintained within the range of about 10° to about 100° C., preferably about 20° to about 90° C. Pressure is not critical herein and any suitable pressure, including elevated pressures, can be employed, but, in general atmospheric, or ambient, pressure is satisfactory.

At the end of the defined treatment the product can be recovered by pouring over ice and filtering or extracting with a suitable solvent. The filter cake or extract can be washed with water and caustic and dried. The resultant product will be essentially free of the ortho nitro aromatic keto compounds originally present.

We believe that during the treatment herein the ortho nitro aromatic keto will be converted to lower benzoic acids, phenolics, carbon dioxide and other caustic-soluble products.

DESCRIPTION OF PREFERRED EMBODIMENTS

The process defined and claimed herein can be illustrated by the following.

EXAMPLE A

A nitrating mixture was prepared by adding gradually 165 grams of 90 weight percent aqueous nitric acid over a period of 30 minutes to 570 grams of oleum containing 22.5 weight percent of sulfur trioxide. During the addition the oleum was continuously stirred and the temperature of the resulting mixture was maintained at about 10° to about 15° C. The first third of the nitric acid addition was highly exothermic, the second third mildly exothermic and the last third essentially non-exothermic. Similarly 200 grams of benzophenone were added over a period of 30 minutes to 1900 grams of oleum containing 22.5 weight percent of sulfur trioxide while maintaining the temperature of the mixture in a temperature range of about 10° to about 20° C. With vigorous stirring and cooling, the nitrating mixture prepared above was gradually added over a period of 1.5 hours to the benzophenone mixture prepared above while maintaining the temperature of the resulting mixture in the range of about 10° to about 15° C. The resulting mixture was permitted to rise to 25° C. and held there for 30 minutes, after which the mixture was heated to 70° C. and maintained at the latter temperature for 30 minutes and then cooled to 25° C. The resulting product was poured over 2,000 grams of a cracked ice-water mixture and filtered. The recovered solids were washed twice with 1000 milliliter portions of water, thereafter with 1000 milliliters of a 10 weight percent aqueous sodium hydroxide solution and finally twice with 1000 milliliter portions of water, until the final washings were found to have a neutral pH value. The solid product was dried in a vacuum oven at 100° C. for 20 hours, resulting in 289 grams of dinitrobenzophenones, corresponding to a yield of 96 percent. Analysis of the product by high performance liquid chromatography (HPLC) showed the presence of the following isomers: 89.1 weight percent m,m'-dinitrobenzophenone, 5.9 weight percent m,p'-dinitrobenzophenone and 5.0 weight percent o,m'-dinitrobenzophenone.

EXAMPLE B

In this example, 200 grams of benzophenone was incrementally added over a period of one hour, while stirring, to 1200 grams of 90 weight percent of aqueous nitric acid while maintaining the temperature during addition between about 65° and 75° C. After addition of benzophenone was complete, the temperature of the mixture was raised to 90° C. and the reaction was permitted to continue at such temperature for three hours. The solution was cooled to room temperature (25° C.) and then poured, while stirring, over 2000 grams of cracked icewater mixture. The precipitated solids were recovered by filtration, washed four times with water (1000 milliliters each time) until the final washings were essentially neutral, and then dried in a vacuum oven for 24 hours at 100° C. The cream-colored product recovered amounted to 299 grams, corresponding essentially to a yield of 100 percent. Analysis of the product by HPLC showed the following isomer distribution: 7.9 weight percent o,o'-dinitrobenzophenone, 29.7 weight percent o,m'-dinitrobenzophenone, 44.4 weight percent m,m'-dinitrobenzophenone, 17.2 weight percent m,p'-dinitrobenzophenone and 0.8 weight percent p,p'-dinitrobenzophenone.

EXAMPLE C

Herein 110 grams of benzophenone was added gradually, over a 30 minute period, while stirring, to 1100 grams of 98 weight percent aqueous sulfuric acid while maintaining the temperature, during the addition, at about 25° C. In another container, a nitrating mixture was prepared by gradually adding, over a 90 minute period, while stirring, 84 grams of 90 weight percent aqueous nitric acid to 276 grams of concentrated sulfuric acid, while maintaining the temperature of the mixture during the addition between about 20° and 25° C. The latter mixture was then added, by way of an addition funnel, to the dissolved benzophenone at a rate sufficient to maintain the temperature of the resulting mixture slightly below about 30° C. Upon completion of the addition, the resulting mixture was allowed to react at 30° C. for 30 minutes and then at 50° C. for 30 minutes, and finally at 70° C. for 30 minutes. The product was cooled and worked up as in Example A, resulting in the production of 163.7 grams of dinitrobenzophenones, essentially 100 percent yield. Analysis of the product by HPLC showed the following: 2.5 weight percent o,o'-dinitrobenzophenone, 20.6 weight percent o,m'-dinitrobenzophenone, 65.2 weight percent m,m'-dinitrobenzophenone, 11.7 weight percent m,p'-dinitrobenzophenone and <0.1 weight percent p,p'-dinitrobenzophenone.

EXAMPLE D

Example A was repeated except that 2400 grams of oleum containing 15 weight percent of sulfur trioxide was used. The product obtained contained the following isomers: 1.6 weight percent o,o'-dinitrobenzophenone, 17.0 weight percent o,m'-dinitrobenzophenone, 71.5 weight percent m,m'-dinitrobenzophenone, 10 weight percent m,p'-dinitrobenzophenone and 1.0 weight percent p,p'-dinitrobenzophenone.

EXAMPLE E

Into a three-liter, three-necked, round-bottomed flask, equipped with a mechanical stirrer, thermowell and an addition funnel, there was added 2550 grams of 85 weight percent of aqueous nitric acid (1610 milliliters of 90 weight percent aqueous nitric acid and 140 milliliters of water), which was then cooled to about 5° to 10° C. To the stirred autoclave there was gradually added 280 grams of 1,1-diphenylethane over a period of 2.5 hours while maintaining the temperature of the mixture during the addition at about 10° C. After the addition was complete, the mixture was permitted to warm up to about 25° C. and stirred for 30 minutes. The mixture was then poured over ice water and extracted with toluene. The organic layer so obtained was washed successively with 500 milliliters of water, 500 milliliters of five weight percent aqueous sodium hydroxide and then with 500 milliliters of water. The resulting product, a nitrated diphenylethane, was dried by contact with magnesium sulfate, filtered, and the filtrate taken to dryness in a rotary evaporator, resulting in 389 grams of a dark red oil, which was partially crystalline.

A total of 135 grams of the nitrated diphenylethane obtained above was charged into a one liter, 316-stainless steel autoclave, followed by 200 grams of water. The autoclave was heated to 170° C. and, while maintaining this temperature, 170 milliliters of 70 percent aqueous nitric acid was added thereto over a period of 1.5 hours. When the addition of acid was completed, the reaction mixture was maintained at this temperature for 0.5 hour, at the end of which time the pressure was 450 pounds per square inch gauge (3.1 MPa). On cooling to about 25° C., followed by filtration, a total of 111 grams of yellow solids were obtained, amounting to a yield of 82.2 percent. Analysis of the product by HPLC showed the following: 57.9 weight percent p,p'-dinitrobenzophenone, 13.3 weight percent m,p'-dinitrobenzophenone, 25 weight percent o,p'-dinitrobenzophenone, 3.0 weight percent o,m'-dinitrobenzophenone and 0.8 weight percent o,o'-dinitrobenzophenone.

EXAMPLE F

A total of 55.7 grams of p-nitrobenzoyl chloride was dissolved in 225 milliliters of benzene and, while stirring, 65 grams of anhydrous aluminum chloride was added thereto over a period of 40 minutes, all of which was done under a nitrogen atmosphere. After addition was completed, the mixture was stirred for 30 minutes on a steam bath and then poured over ice. Extraction of the resulting product with methylene chloride, followed by washing the organic layer with water, drying with anhydrous magnesium sulfate and filtering, resulted in the recovery of 62.2 grams of p-nitrobenzophenone.

A total of 10 grams of p-nitrobenzophenone was dissolved in 50 milliliters of oleum containing 20 weight percent sulfur trioxide and then nitrated with a mixture containing 3.2 grams of 90 percent aqueous nitric acid and 15 grams of oleum containing 20 weight percent sulfur trioxide for 45 minutes at 15° C. The product was worked up, as before, and had the following composition: 84.1 weight percent m,p'-dinitrobenzophenone, 3.6 weight percent p,p'-dinitrobenzophenone and 12.3 weight percent o,p'-dinitrobenzophenone.

EXAMPLE G

The run of Example E was repeated but wherein 1,1-diphenylmethane was employed in place of 1,1-diphenylethane. On workup a 90 percent yield of a dinitrodiphenylmethane product was obtained.

This product was oxidized following the procedure of Example E to obtain an 85 percent yield of dinitrobenzophenones analyzing as follows: 44.9 weight percent p,p'-dinitrobenzophenone, 11.3 weight percent m,p'-dinitrobenzophenone, 31.0 weight percent o,p'-dinitrobenzophenone, 6.1 weight percent o,m'-dinitrobenzophenone and 6.1 weight percent o,o'-dinitrobenzophenone.

EXAMPLE H

Five grams of p-chlorobenzophenone was added, while stirring, to 50 milliliters of 90 percent aqueous nitric acid, while being maintained at 10° C. The mixture was permitted to come to room temperature (25° C.) and was left standing for 16 hours. The mixture was then poured over ice, filtered, washed with water until neutral, resulting in 6.0 grams of product. Analysis of the product by HPLC showed the following: 62.2 weight percent m-nitro-p'-chlorobenzophenone, 8.3 weight percent p-nitro-p'-chlorobenzophenone and 29.5 weight percent o-nitro-p'-chloro-benzophenone.

EXAMPLE I

A two-liter flask equipped with a mechanical stirrer and thermometer was charged with 250 grams of benzoin and 930 milliliters of acetic anhydride. After cooling to 15° C., 400 milliliters of concentrated sulfuric acid was added dropwise thereto while maintaining the temperature at about 30° C. The flask was cooled to −20° C. and 60 milliliters of 90 weight percent aqueous nitric acid was added at a rate to maintain the temperature of the flask between about −20° and −10° C. After the addition was complete the mixture was allowed to come to about 25° C. and stand overnight. No crystals formed, even when a seed crystal was added thereto. The mixture was poured into about 450 grams of ice water, and the aqueous portion was decanted from the gummy solid which was washed twice, each time with 500 milliliters of water. The solid recrystallized once from an equal volume of methanol and a second time from two volumes of methanol. Analysis by gas chromatography showed the material to be about 90 percent pure at this point. The solids were then slurried with an equal volume of methanol and filtered hot (50° C.). Air drying resulted in 577 grams of a white solid having a melting point to 124° to 126° C. and better than 98 percent pure p-nitrobenzoin acetate. From the filtrate a second crop of product was obtained analyzing by HPLC as follows: 36.8 weight percent p-nitro, 5.7 weight percent m-nitro and 57.5 weight percent o-nitro benzoin acetates. Thirty grams of the second crop obtained above was added to 100 milliliters of 70 weight percent aqueous nitric acid and heated at 70° C. for one hour. The reaction mixture was cooled to about 25° C. and then poured over 300 grams of an ice water mixture. After extraction with 300 milliliters of methylene chloride, washing the organic layer with 300 milliliters of water, drying over magnesium sulfate and filtration, followed by evaporation of the filtrate to dryness, afforded 24.1 grams of a yellow product. Analysis by gas liquid chromatography showed the following: 55 weight percent of o-nitrobenzil, 6.4 weight percent m-nitrobenzil and 38.6 p-nitrobenzil.

Each of the product mixtures obtained above, as well as two blends, was mixed while stirring with sulfuric acid or oleum for selected periods of time at selected temperature levels. The treated materials were then quenched by pouring over ice and filtered or extracted. The recovered products were washed successively with water, 10 weight percent aqueous sodium hydroxide and water and then dried and analyzed by HPLC. The data obtained are summarized below in Table I.

TABLE I

| Example | Source of Material Being Treated | Grams of Such Material Treated | $H_2SO_4$, Grams | $SO_3$, Grams | Weight Percent $SO_3$ In $H_2SO_4$ | Temp., °C. | Time, Hrs. | Product Recovered, Grams | | Isomer Distribution, Weight Percent | | | | | |
|---|---|---|---|---|---|---|---|---|---|---|---|---|---|---|---|
| | | | | | | | | | | o,o' | o,m' | o,p' | m,m' | m,p' | p,p' |
| I | A | 10 | 92 | 0 | 0 | 70 | 0.5 | * | Initial | 0 | 5.0 | 0 | 89.1 | 5.9 | 0 |
| | | | | | | | | | Final | 0 | 5.0 | 0 | 89.1 | 5.9 | 0 |
| II | A | 10 | 92 | 0 | 0 | 100 | 0.5 | 9.4 | Initial | 0 | 5.0 | 0 | 89.1 | 5.9 | 0 |

TABLE I-continued

| Example | Source | H2SO4 | SO3 | Wt% SO3 in H2SO4 | Temp °C | Time Hrs | Product g | | o | m | p | other |
|---|---|---|---|---|---|---|---|---|---|---|---|---|
| III | A | 50 | 160 | 40 | 20 | 70 | 1.0 | 45 | Initial | 0 | 5.0 | 0 | 89.1 5.9 0 |
| | | | | | | | | | Final | 0 | 5.2 | 0 | 89.0 5.8 0 |
| | | | | | | | | | | 0 | 0 | 0 | 93.6 6.4 0 |
| IV | B | 50 | 160 | 40 | 20 | 70 | 0.5 | * | Initial | 7.9 | 29.7 | 0 | 44.4 17.2 0.8 |
| | | | | | | | | | Final | 0 | 0 | 0 | 67.7 30.0 2.3 |
| V | B | 50 | 170 | 30 | 15 | 70 | 0.5 | 29.0 | Initial | 7.9 | 29.7 | 0 | 44.4 17.2 0.8 |
| | | | | | | | | | Final | 0 | 0 | 0 | 69.5 30.5 0 |
| VI | C | 50 | 170 | 30 | 15 | 70 | 1.0 | * | Initial | 2.5 | 20.6 | 0 | 65.2 11.7 <0 |
| | | | | | | | | | Final | 0 | 0 | 0 | 85.0 15.0 0 |
| VII | D | 30 | 570 | 30 | 5 | 90 | 1.0 | 25.5 | Initial | 1.6 | 17.0 | 0 | 71.5 10.0 1.0 |
| | | | | | | | | | Final | 0 | 14.7 | 0 | 77.3 8.0 0 |
| VIII | E | 50 | 323 | 57 | 15 | 70 | 1.0 | 31.1 | Initial | 0.8 | 3.0 | 25.0 | 0 13.3 57.9 |
| | | | | | | | | | Final | 0 | 0 | 0 | 0 18.3 81.7 |
| IX | F | 12 | 100 | 16 | 14 | 70 | 0.5 | * | Initial | 0 | 0 | 12.3 | 0 84.1 3.6 |
| | | | | | | | | | Final | 0 | 0 | 0.5 | 0 95.5 4.0 |
| X | F | 12 | 100 | 16 | 14 | 70 | 1.0 | 10.5 | Initial | 0 | 0 | 12.3 | 0 84.1 3.6 |
| | | | | | | | | | Final | 0 | 0 | 0 | 0 96.0 4.0 |
| XI | G | 50 | 323 | 57 | 15 | 70 | 1.0 | * | Initial | 6.1 | 6.1 | 31.0 | 0 11.3 44.9 |
| | | | | | | | | | Final | 0 | 0 | 0 | 0 19.9 80.1 |

| Example | Source of Material Being Treated | Grams of such Material Treated | H2SO4, Grams | SO3, Grams | Weight Percent SO3 In H2SO4 | Temp., °C. | Time, Hrs. | Product Recovered, Grams | | Isomer Distribution, Weight Percent | | |
|---|---|---|---|---|---|---|---|---|---|---|---|---|
| | | | | | | | | | | o | m | p |
| XII | H | 6 | 45.6 | 11.4 | 20 | 70 | 0.1 | 2.7 | Initial | 29.5 | 62.2 | 8.3 |
| | | | | | | | | | Final | 0 | 88.0 | 12.0 |
| XIII | I | 2.6 | 40.5 | 4.5 | 10 | 50 | 0.3 | * | Initial | 55.0 | 6.4 | 38.6 |
| | | | | | | | | | Final | 0 | 10.5 | 89.5 |
| XIV | Blend of Mononitro-benzophenones | 10 | 80 | 20 | 20 | 70 | 1.0 | 5.1 | Initial | 40.0 | 60.0 | 0 |
| | | | | | | | | | Final | 0 | 100 | 0 |
| XV | Blend of Nitroaceto-phenones | 10 | 80 | 20 | 20 | 25 | 1.0 | 6.7 | Initial | 20.0 | 70.0 | 10.0 |
| | | | | | | | | | Final | 0 | 89.8 | 10.2 |

*Not determined.

The data in the above table clearly exemplifies the process defined and claimed herein. In each of Examples I and II, wherein the isomeric mixture was contacted solely with sulfuric acid, the ortho nitro aromatic ketone content thereof remained unchanged. However, when in each of the remaining examples the substrates containing various ortho nitro aromatic ketone compounds were contacted with oleum, as defined and claimed herein, the ortho nitro aromatic keto content thereof was substantially reduced, in most cases with the complete disappearance thereof.

Obviously, many modifications and variations of the invention, as hereinabove set forth, can be made without departing from the spirit and scope thereof and, therefore, only such limitations should be imposed as are indicated in the appended claims.

We claim:

1. A process for reducing the amount of ortho nitro aromatic keto compounds in a mixture containing the same which comprises contacting said mixture with oleum.

2. The process of claim 1 wherein said ortho nitro aromatic keto compounds are defined by the following formula:

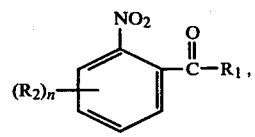

wherein $R_1$ can be an alkyl radical having from one to 10 carbon atoms, an aryl radical having from six to 20 carbon atoms or an aroyl radical having from six to 20 carbon atoms, $R_2$ can be a halogen, nitro, cyano or an alkyl, aryl or aroyl radical as defined above, and n is an integer ranging from 0 to 4.

3. The process of claim 2 wherein $R_1$ can be an alkyl radical having from one to four carbon atoms, an aryl radical having from six to 10 carbon atoms, or an aroyl radical having from six to 10 carbon atoms, $R_2$ can be a halogen, nitro, cyano or an alkyl radical having from one to four carbon atoms or an aryl radical having from six to 10 carbon atoms and n is an integer from 0 to 2.

4. The process of claim 1 wherein said mixture is an isomeric mixture of dinitrobenzophenones.

5. The process of claim 1 wherein said mixture is an isomeric mixture of chloronitrobenzophenones.

6. The process of claim 1 wherein said mixture is an isomeric mixture of mononitrobenzophenones.

7. The process of claim 1 wherein said mixture is an isomeric mixture of nitroacetophenones.

8. The process of claim 1 wherein said mixture is an isomeric mixture of nitrobenzils.

9. The process of claim 1 wherein the weight ratio of said ortho nitro aromatic keto compounds to the remainder of said mixture is in the range of about 0.1:99 to about 60:40.

10. The process of claim 1 wherein the weight ratio of said ortho nitro aromatic keto compounds to the remainder of said mixture is in the range of about 5:95 to about 40:60.

11. The process of claim 1 wherein the oleum contains from about five to about 65 weight percent sulfur trioxide.

12. The process of claim 1 wherein the oleum contains from about 10 to about 35 weight percent sulfur trioxide.

13. The process of claim 1 wherein the weight ratio of oleum to said mixture is in the range of about 1:1 to about 25:1.

14. The process of claim 1 wherein the weight ratio of oleum to said mixture is in the range of about 2:1 to about 5:1.

15. The process of claim 1 wherein said contact is effected at a temperature of about 10° to about 100° C. for about 0.1 to about 48 hours.

16. The process of claim 1 wherein said contact is effected at a temperature of about 20° to about 90° C. for about 0.5 to about six hours.

* * * * *